US010945587B2

(12) United States Patent
Fanenbruck et al.

(10) Patent No.: US 10,945,587 B2
(45) Date of Patent: Mar. 16, 2021

(54) ENDOSCOPIC PROBE WITH REDUCED OBSTRUCTION

(71) Applicant: Carl Zeiss Meditec AG, Jena (DE)

(72) Inventors: Martin Fanenbruck, Oberkochen (DE); Helge Jess, Oberkochen (DE); Roland Guckler, Ulm (DE)

(73) Assignee: CARL ZEISS MEDITEC AG, Jena (DE)

( * ) Notice: Subject to any disclaimer, the term of this patent is extended or adjusted under 35 U.S.C. 154(b) by 367 days.

(21) Appl. No.: 15/950,715

(22) Filed: Apr. 11, 2018

(65) Prior Publication Data

US 2018/0303318 A1    Oct. 25, 2018

(30) Foreign Application Priority Data

Apr. 19, 2017    (DE) .................. 10 2017 108 272.7

(51) Int. Cl.
*A61B 1/00*    (2006.01)
*A61B 1/07*    (2006.01)

(52) U.S. Cl.
CPC ...... *A61B 1/00066* (2013.01); *A61B 1/00016* (2013.01); *A61B 1/00114* (2013.01); *A61B 1/07* (2013.01); *A61B 1/00112* (2013.01)

(58) Field of Classification Search
CPC ............ A61B 1/00066; A61B 1/00105; A61B 1/00114; A61B 1/00112; A61B 1/00071; A61B 1/0669; A61B 1/042
See application file for complete search history.

(56) References Cited

U.S. PATENT DOCUMENTS

| 4,148,550 | A | * | 4/1979 | MacAnally ............ A61B 1/002 359/435 |
| 4,617,915 | A | | 10/1986 | Arakawa |
| 5,184,602 | A | | 2/1993 | Anapliotis et al. |
| 6,413,208 | B1 | | 7/2002 | Schöllhorn et al. |
| 7,162,292 | B2 | | 1/2007 | Ohno et al. |

(Continued)

FOREIGN PATENT DOCUMENTS

| DE | 10 2015 004 546 | 10/2016 |
| EP | 0 369 937 | 5/1990 |

(Continued)

OTHER PUBLICATIONS

German Office Action for 10 2017 108 272.7 dated Apr. 19, 2017.
European Search Report for 18167322.9 dated Aug. 13, 2018.

*Primary Examiner* — John P Leubecker
(74) *Attorney, Agent, or Firm* — Nixon Peabody LLP; Jeffrey L. Costellia

(57) ABSTRACT

An endoscopic probe includes a handle with a front end, a rear end with a rear end axis and, extending between the front end and the rear end, a straight grip portion with a grip portion axis. The probe further includes a shaft extending from the front end of the handle and having a shaft axis, and a cable issuing from the rear end. The shaft axis, the rear end axis and the grip portion axis lie within a common plane. The shaft axis encloses an angle in the range of 100 to 140 degrees with the grip portion axis, the grip portion axis encloses an angle in the range of 110 to 130 degrees with the rear end axis, and the shaft axis encloses an angle in the range of 30 to 90 degrees with the rear end axis.

18 Claims, 4 Drawing Sheets

(56) References Cited

U.S. PATENT DOCUMENTS

| | | | |
|---|---|---|---|
| 2001/0018551 A1* | 8/2001 | Komi | A61B 1/0052 600/131 |
| 2003/0149339 A1 | 8/2003 | Ishibiki | |
| 2006/0004258 A1 | 1/2006 | Sun et al. | |
| 2011/0046441 A1* | 2/2011 | Wiltshire | A61B 1/313 600/104 |
| 2011/0178395 A1 | 7/2011 | Miesner et al. | |
| 2011/0257481 A1* | 10/2011 | Ogawa | G02B 23/2484 600/109 |
| 2012/0165605 A1* | 6/2012 | Yamazaki | G02B 23/2476 600/106 |
| 2012/0289858 A1* | 11/2012 | Ouyang | A61B 1/00124 600/562 |
| 2014/0052131 A1 | 2/2014 | Busch-Madsen et al. | |
| 2014/0107416 A1* | 4/2014 | Birnkrant | A61B 1/00057 600/110 |
| 2014/0121458 A1* | 5/2014 | St. George | A61B 1/00085 600/107 |
| 2014/0324012 A1* | 10/2014 | Wald | A61M 1/0047 604/500 |
| 2015/0164502 A1 | 6/2015 | Richard et al. | |
| 2016/0242629 A1* | 8/2016 | Hijihara | A61B 1/0052 |
| 2016/0296103 A1 | 10/2016 | Gotz et al. | |
| 2017/0042408 A1 | 2/2017 | Washburn et al. | |
| 2017/0086651 A1 | 3/2017 | Sato et al. | |
| 2017/0354319 A1 | 12/2017 | Sato et al. | |
| 2019/0191966 A1* | 6/2019 | Hijihara | A61B 1/0052 |
| 2019/0374236 A1* | 12/2019 | Weitzman | A61B 17/1631 |

FOREIGN PATENT DOCUMENTS

| | | |
|---|---|---|
| EP | 2883504 | 6/2015 |
| EP | 3248533 | 11/2017 |

* cited by examiner

ENDOSCOPIC PROBE WITH REDUCED OBSTRUCTION

The present application claims priority to German Application No. 10 2017108 272.7 filed Apr. 19, 2017, the disclosure of which is hereby incorporated by reference herein in its entirety.

BACKGROUND OF THE INVENTION

Field of the Invention

The present invention relates to an endoscopic probe with a shaft and a handle, which comprises a front end, a rear end and, extending between the front end and the rear end, a grip portion.

Description of Related Art

In microsurgery, for instance in neurosurgery, it is generally necessary, for example after removal of a deep-lying tumour or after treatment of an aneurysm, to view sites that lie outside the line of vision of a surgical microscope. For this purpose, endoscopic probes are then used in addition to the surgical microscope, for example endoscopic probes of the kind described in DE 10 2015 004 546 A1, U.S. Pat. No. 7,162,292 B2 and US 2011/0178395 A1.

Endoscopic probes typically have a handle, from one end of which a shaft extends, and from the other end of which a cable emerges. The challenge is to design the endoscopic probe such that, on the one hand, it is highly ergonomic and, on the other hand, it is possible to reliably avoid collision between the endoscopic probe and a surgical microscope that is used together with it.

SUMMARY OF THE INVENTION

The object of the present invention is to make available an endoscopic probe which is highly ergonomic and with which it is possible to reliably avoid collision with a surgical microscope that is used together with said endoscopic probe.

This object is achieved by an endoscopic probe according to Claim 1. The dependent claims contain advantageous embodiments of the invention.

An endoscopic probe according to the invention comprises a handle with a front end, a rear end with a rear end axis and, extending between the front end and the rear end, a straight grip portion with a grip portion axis. Moreover, it comprises a shaft extending from the front end of the handle and having a shaft axis and, when the rear end is designed as a cable outlet end, it has a cable emerging from the rear end. The axes are each defined by the connecting line between the centre points of the cross sections at the ends of the respective portion or of the shaft. In the endoscopic probe according to the invention, the shaft axis, the rear end axis and the grip portion axis lie within one plane. The shaft axis encloses with the grip portion axis an angle in the range of 100 to 140 degrees, in particular in the range of 110 to 130 degrees and preferably in the range of 115 to 125 degrees. The grip portion axis encloses with the rear end axis an angle in the range of 110 to 130 degrees, in particular in the range of 115 to 125 degrees, and the shaft axis encloses with the rear end axis an angle in the range of 30 to 90 degrees. The angle that the shaft axis encloses with the grip portion axis can in particular be the same size as the angle that the grip portion axis encloses with the rear end axis. If present, the cable emerges from the rear end at an angle of not more than a maximum of 20 degrees, preferably not more than 10 degrees with respect to the rear end axis. In particular, the cable can emerge from the rear end in a manner parallel to the rear end axis. In the case of a cable-free endoscopic probe, the rear end can contain an antenna and/or an accumulator.

The angled arrangement of the endoscopic probe according to the invention, at the stated angles, allows the total length in the direction of the grip portion axis to be kept short and at the same time minimizes the risk of the handle, or of the rear end or cable outlet, colliding with a simultaneously used surgical microscope, while a high level of ergonomic comfort is achieved at the same time. Although an angle of 90 degrees between the shaft axis and the handle axis would be optimal in the sense of minimizing the risk of collision, it has been found that such an angle does not permit good manageability in the predominantly one-handed use of the endoscopic probe. In particular, an angle of 90 degrees adversely affects the rotation in situ and the safe insertion of the probe. The angle according to the invention, between the shaft axis and the handle axis, i.e. the grip portion axis, in the range of 100 to 140 degrees, in particular in the range of 110 to 130 degrees and preferably in the range of 115 to 125 degrees, permits uncomplicated rotation of the shaft in situ and safe insertion into the site without at the same time substantially increasing the risk of collision with the simultaneously used surgical microscope. By virtue of the fact that the rear end axis is likewise at an angle, specifically in a range of between 110 and 130 degrees, in particular between 115 and 125 degrees, it is possible to avoid a situation where the rear end or the cable collides with the surgical microscope during the rotation of the shaft in situ or during the insertion of the shaft. At the same time, by virtue of the chosen angle of the rear end axis, the cable can be guided across the back of the hand such that it does not unnecessarily impede the user during the rotation of the probe in situ. The stated angles therefore characterize a particularly advantageous geometry of the endoscopic probe.

In the endoscopic probe according to the invention, the shaft can have a length in the range of 50 to 180 mm, in particular of 90 to 130 mm. This is long enough for use in microsurgical interventions, but also short enough to be able to avoid collision of the handle with the surgical microscope during the handling of the endoscopic probe.

The shaft can have diameters in the range of 3.0 to 4.1 mm, in particular in the range of 3.4 to 3.8 mm. The shaft, at least in a distal portion, can have a wall thickness in the range of 0.3 to 0.5 mm, in particular in the range of 0.35 to 0.45 mm. At a proximal portion of the shaft adjoining the front end of the handle, the shaft can have an increased wall thickness in the range of 1.3 to 1.5 mm, in particular in the range of 1.35 to 1.45 mm. The proximal portion can have a length in the range of 10 to 20 mm, in particular in the range of 13 to 17 mm. A shaft with the stated dimensions is small enough to permit a surgical intervention that is as non-invasive as possible, but also stable enough to avoid damage to the shaft during a surgical procedure. Moreover, the clear shaft diameter is large enough to permit a high image quality and a high resolution of images captured through the shaft. In particular, the interior of the shaft can then accommodate an image-conveying optics system with which object light emanating from an object observed by means of the endoscopic probe is conveyed to an image sensor arranged in the handle, which is preferably an HD sensor. Moreover, there is still enough room in the shaft to ensure that illumination light, which is emitted from a light source arranged in the interior of the handle and with which the object observed by means of the endoscopic probe is illuminated, can be guided to the observed object with the aid of an optical fibre routed through the interior of the shaft.

The handle of the endoscopic probe according to the invention can have a diameter of 18 to 38 mm, in particular of 24 to 32 mm. Moreover, the grip portion and the front end can together have a length in the range of 100 to 120 mm, in particular in the range of 105 to 115 mm. With these dimensions, it is compact enough to allow the endoscopic probe to be used together with a surgical microscope, without there being any appreciable risk of the handle colliding with the surgical microscope, but also large enough to be able to receive the necessary technical elements such as light source and sensor, but also a heat accumulator to prevent the handle from overheating at places, which would make handling uncomfortable or, in extreme cases, impossible. Moreover, the safe handling of an instrument with the described geometry likewise requires a grip or handle of the stated dimensions.

In an advantageous further embodiment of the endoscopic probe according to the invention, the grip portion of the handle, in a plane perpendicular to the common plane of the shaft axis, the grip portion axis and the rear end axis, has a cross section with a cross-sectional upper side, which faces the point of intersection of an imaginary continuation of the shaft axis with an imaginary continuation of the rear end axis, and a cross-sectional underside facing away from this intersection. The cross-sectional upper side has a central and preferably convex portion and, adjoining the central portion, two portions which are less convex or concave or which are straight and which form cut-outs from the limbs of an imaginary isosceles triangle whose apex lies centrally above the cross-sectional upper side. The isosceles triangle can in particular be an equilateral triangle. This embodiment of the grip portion of the endoscopic probe is based on the recognition that the grip portion is generally not grasped in the whole hand, and instead is often gripped with the finger tips like a violin bow in order to permit improved fine-motor handling, or lies in the crook between thumb and index finger, balanced on the middle finger and guided with the tips of thumb and index finger. The straight portions of the cross-sectional upper side form advantageous grip surfaces for gripping the grip portion with the tip of the thumb on one side and with the tips of generally at least the index finger, and possibly the middle finger, on the other side. With the aid of the straight portions serving as grip surfaces or grip structures in the grip portion, it is possible to ensure safe handling and ergonomic guiding of the endoscopic probe. The symmetry in the form of an isosceles triangle means that the endoscopic probe is suitable both for safe handling with the left hand and also for safe handling with the right hand.

The cross-sectional underside of the cross section of the grip portion can have a convexity, wherein the cross-sectional underside then has a central region with a central convexity and, adjoining the central region, portions that have a lesser convexity compared to the central convexity. In particular, the portions that have a lesser convexity or concavity compared to the central convexity can also be free of convexity and/or can extend parallel to each other. By the reduction of the convexity, and in particular if the portions of lesser convexity are formed entirely without convexity as parallel portions, relatively sharp edges can be formed at the margins of these portions and can contribute to the safe handling and guiding of the endoscopic probe.

The cross-sectional underside can additionally have a bearing surface for the middle finger. This surface can be embodied, for example, in the form of a shallow portion of the cross-sectional underside or in the form of an indent or dimple in the cross-sectional underside.

In order as far as possible not to impede the view of the distal end of the shaft, it is advantageous if the shaft is arranged at the front end of the handle in such a way that the front end, perpendicularly with respect to the direction of extent of the shaft axis, has a maximum protrusion, over the shaft, that is dimensioned such that the angle θ between an imaginary line emerging from the distal end of the shaft, extending in the plane of the shaft axis, the rear end axis and the grip portion axis and tangent to the front end of the handle is not more than 8 degrees, preferably not more than 5 degrees. There is also the possibility that the axis of the front end of the handle does not coincide with the shaft axis and that instead the two axes are at an angle to each other that is chosen such that the protrusion of the front end is compensated at the distal end of the shaft, with the result that the angle θ can be further reduced and in particular can be zero degrees.

In the endoscopic probe according to the invention, the shaft and the handle, including the connection between the shaft and the handle, can be impervious to liquid and gas, and the shaft and the handle can be made of a material that can be autoclaved. By means of this embodiment, the shaft and the handle can be sterilized in an autoclave. This embodiment is suitable in particular for endoscopic probes that have no cables. In endoscopic probes with cables, the cable and the connection between the cable and the handle are also impervious to liquid and gas, and the cable is made of a material that can be autoclaved. By means of this embodiment, endoscopic probes with cables can also be sterilized in an autoclave. The sterilizability dispenses with the need to use a drape, such that ergonomic handling is in any case maintained.

Further features, properties and advantages of the present invention will become apparent from the following description of an exemplary embodiment with reference to the accompanying figures.

DETAILED DESCRIPTION OF THE INVENTION

Figure 1:
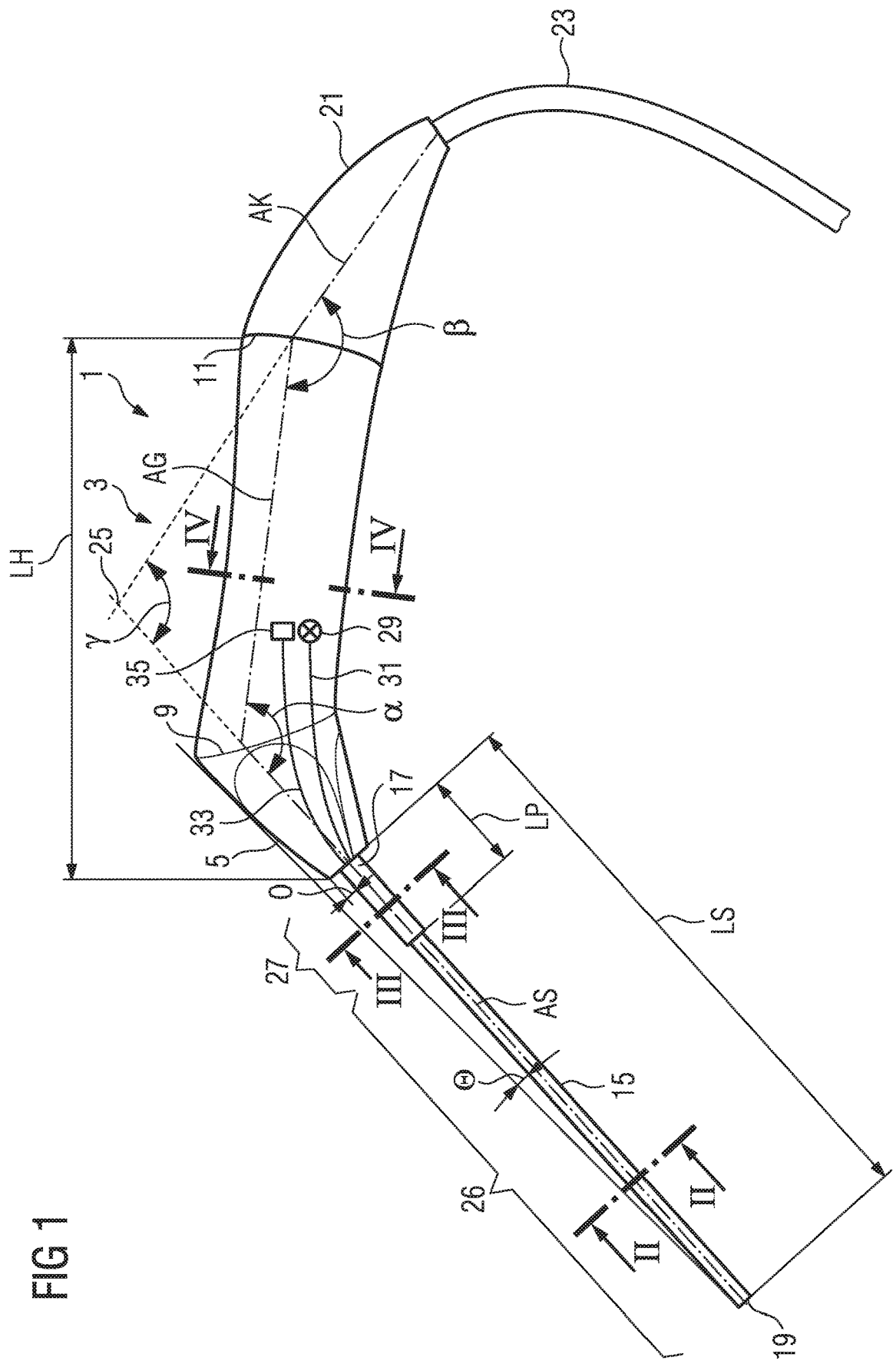
FIG. 1 shows an exemplary embodiment of an endoscopic probe with a handle and a shaft.
Figure 2:
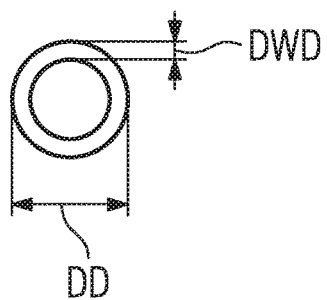
FIG. 2 shows a section through the shaft along the line II-II in FIG. 1.
Figure 3:
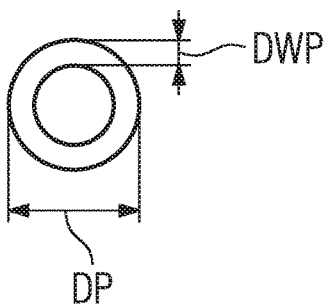
FIG. 3 shows a section through the shaft along the line III-III in FIG. 1.
Figure 4:
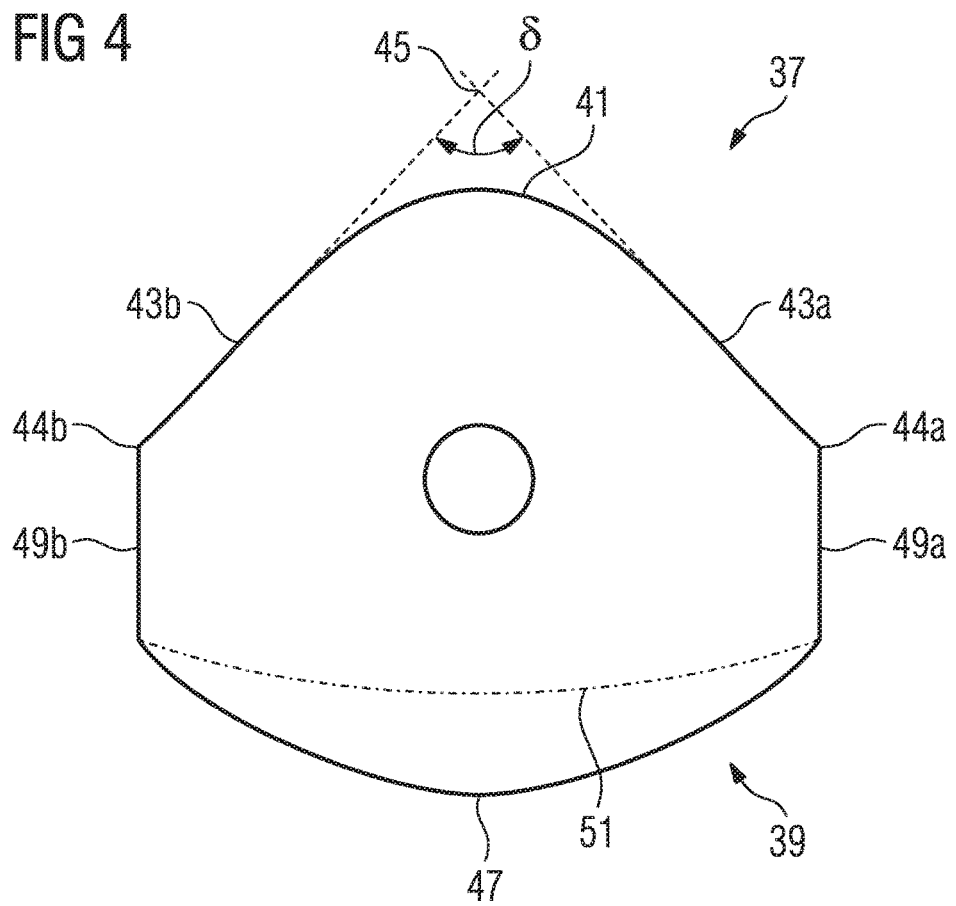
FIG. 4 shows a section through the handle along the line IV-IV in FIG. 1.

An exemplary embodiment of an endoscopic probe according to the invention is explained below with reference to FIGS. 1 to 4. FIG. 1 shows a view of the endoscopic probe with a handle and a shaft, and FIGS. 2 to 4 show cross sections through the shaft or handle.

In the present exemplary embodiment, the endoscopic probe comprises a handle 1 with a grip portion 3, a front end 5 and a rear end 21. The grip portion 3 extends along a grip portion axis AG, wherein the grip portion axis interconnects the centre points of the two end faces 9, 11 of the grip portion 3. The end face 9 of the grip portion is adjoined by a front end 5, from which the shaft 15 extends along a shaft axis AS. The shaft 15, which is straight in the present exemplary embodiment, has a proximal end 17, which adjoins the front end 5 of the handle 1, and a distal end 19, which is remote from the front end 5 of the handle 1. In the present exemplary embodiment, its shaft axis AS encloses an angle α of 130 degrees with the grip portion axis AG. However, it will be noted at this point that this angle α does not necessarily have to be 130 degrees, and instead it can lie in a range of 100 to 140 degrees, in particular in a range of 110 to 130 degrees, and preferably in a range of 115 to 125 degrees. This range, and in particular the narrower of the two ranges, has proven advantageous in terms of ergonomics.

The other end face 11 of the grip portion 3 is adjoined by the rear end 21 of the handle 1, where a cable 23 emerges from the handle 1 in the present exemplary embodiment. The rear end 21 has a rear end axis AK, wherein the rear end axis AK extends through the centre point of the cross-sectional surface adjoining the end face 11 of the grip portion and through the centre point of the surface of emergence of the cable 23. The cable 23 preferably emerges from the rear end 21 in a direction that corresponds to the direction of the rear end axis AK. However, it can in principle also emerge at a small angle with respect to the rear end axis AK, wherein the small angle is not more than a maximum of 20 degrees, preferably not more than 10 degrees.

In the present exemplary embodiment, the rear end axis AK encloses an angle β of 130 degrees with the grip portion axis AG. However, it will be noted at this point that, in other design variants, the angle β can lie in the range of between 110 and 130 degrees, preferably in the range of between 115 and 125 degrees. The range of 110 to 130 degrees, and in particular the range of 115 to 125 degrees, has proven advantageous in terms of ergonomics.

The shaft axis AS, the grip portion axis AG and the rear end axis AK lie in a common plane, as a result of which the imaginary continuations of the shaft axis AS and of the rear end axis AK intersect at a point of intersection 25. The imaginary continuations of the two axes are indicated by broken lines in FIG. 1. In the present exemplary embodiment, they enclose an angle γ of 80 degrees. Here too, however, the angle γ does not necessarily have to be 80 degrees, and instead it can lie in a range of between 30 and 90 degrees, for example it can be 60 degrees. Said ranges for the angle γ are based on the aforementioned angle ranges for the angles α and β. By virtue of the fact that all three axes AS, AG and AK lie in a common plane, the endoscopic probe can be configured such that it can be guided equally advantageously both with the left hand and also with the right hand.

In the present exemplary embodiment, the grip portion 3 together with the front end 5 has a length LH of 110 mm. However, it is also possible to deviate from this value. Possible lengths of the grip portion 3 including the front end 5 can lie in the range of between 100 and 120 mm.

In the present exemplary embodiment, the shaft 15 has a length LS of 120 mm from the proximal end 17 to the distal end 19. Here too, it should be noted that, in other design variants of the endoscopic probe, the shaft length LS can have another value in a range of 50 to 180 mm, in particular in the range of 90 to 130 mm. The external diameter DD of the shaft (see also FIG. 2, which shows a section along the line II-II from FIG. 1) is 3.6 mm in a distal portion 26 of the shaft 15, and the wall thickness DWD in the distal portion 26 is 0.4 mm. In other design variants of the endoscopic probe according to the invention, the external diameter DD and the wall thickness DWD in the distal portion 26 of the shaft 15 can also assume other values, wherein the values for the external diameter DD lie in the range of between 3.0 and 4.1, in particular in the range of 3.4 to 3.8 mm, and the values for the wall thickness DWD lie in the range of between 0.4 and 0.5 mm, in particular in the range of 0.35 to 0.45 mm. In a proximal portion 27 located between the distal portion 26 and the proximal end 17 of the shaft 15 (see also FIG. 3, which shows a section along the line III-III from FIG. 1), the shaft has an increased wall thickness DWP, which is 1.4 mm in the present exemplary embodiment, and which in other design variants of the endoscopic probe according to the invention can be in the range of 1.3 to 1.5 mm, in particular in the range of 1.35 to 1.45 mm. Since the internal diameter of the shaft is the same along the entire length of the shaft, the external diameter DP of the shaft 15 is correspondingly increased in the proximal portion 27. In the present example, the proximal portion extends over a length LP of 15 mm, although in other design variants it can also assume other values in the range of between 10 and 20 mm, in particular in the range of 13 to 17 mm. The stability of the shaft is increased by the strengthening in the proximal portion. It is thus possible to obtain a shaft which has a high degree of stability while at the same time having a small diameter in the distal portion and a large aperture.

Said diameters and wall thicknesses of the shaft 15 are chosen such that they on the one hand allow the shaft to be inserted into narrow operating channels, while the shaft on the other hand still has sufficient stability to ensure that it is not damaged during handling. Moreover, the internal diameter of the shaft is large enough to, on the one hand, allow passage of an optical fibre 31, with which light from a light source 29 arranged in the handle 1 can be conveyed to the distal end 19 of the shaft 15, and, on the other hand, light reflected from the object observed by means of the endoscopic probe can be conveyed to a digital image sensor 35, for example a CCD sensor or a CMOS sensor, via an image-conveying optics system, which in the present case is configured as a coherent fibre bundle 33. Alternatively, there is also the possibility for the optics system to be configured in the form of lens combinations. In particular, the dimensions of the shaft allow it to receive an image-conveying optics system which permits the capture of HD videos by means of the digital image sensor 35. It is likewise possible to arrange the digital image sensor 35 on or in the distal tip of the shaft 15.

To permit ergonomic handling of the endoscopic probe by a person using the probe, the grip portion 3 of the handle 1 has a special cross section. This cross section is depicted in FIG. 4, which shows a section along the line IV-IV in FIG. 1. The cross section lies in a plane which extends perpendicularly with respect to the common plane of the shaft axis AS, the grip portion axis AG and the rear end axis AK. The cross section shown in FIG. 4 has a cross-sectional upper side 37 and a cross-sectional underside 39. In the grip portion 3, the cross-sectional upper side 37 forms the side of the grip portion on which lies the point of intersection 25 between the imaginary continuations of the shaft axis AS and of the rear end axis AK.

In the endoscopic probe according to the invention, the cross-sectional upper side 37 has a convex central portion 41 and, adjoining the latter, two portions 43a, 43b which, in the present exemplary embodiment, are slightly convex. The convexities can vary along the grip portion axis AG. The tangents to the slightly convex portions 43a, 43b form cut-outs from the limbs of an imaginary isosceles triangle whose apex lies centrally above the cross-sectional upper side 37. The angle δ at the apex is in the range of between 45 and 75 degrees and, in the present exemplary embodiment, measures 60 degrees, at least in a region of the grip portion. The surfaces of the grip portion 3 that are formed by the slightly convex portions 43a, 43b of the cross-sectional upper side represent gripping surfaces at which the grip portion can be gripped with the thumb and with the tip of the index finger.

In the present exemplary embodiment, the cross-sectional underside 39 has a central region 47 with a central convexity, adjoined on both sides by portions 49a, 49b which have a lesser convexity compared to the central convexity, i.e. a convexity with a greater radius of curvature. In the present exemplary embodiment, the radius of curvature is very great, such that the regions 49a, 49b have no convexity at all. The regions 49a, 49b extend symmetrically with respect to the axis of symmetry of the imaginary isosceles triangle of the cross-sectional upper side 37. At the connections of the straight portions 49a, 49b of the cross-sectional underside to the straight portions 43a, 43b of the cross-sectional upper side, it is in this way possible to obtain relatively sharp edges 44a, 44b which can form a tactile marking and thereby contribute to safety in the handling of the endoscopic probe.

In the present exemplary embodiment, a bearing surface for the middle finger can be provided on the side of the grip portion 3 formed by the cross-sectional underside 39, on which bearing surface the middle finger can rest. This bearing surface can be a region of the grip portion 3 in which the central region of the cross-sectional underside 39 has a flatter convexity, as is indicated by the broken line 51 in FIG. 4.

Figure 5:
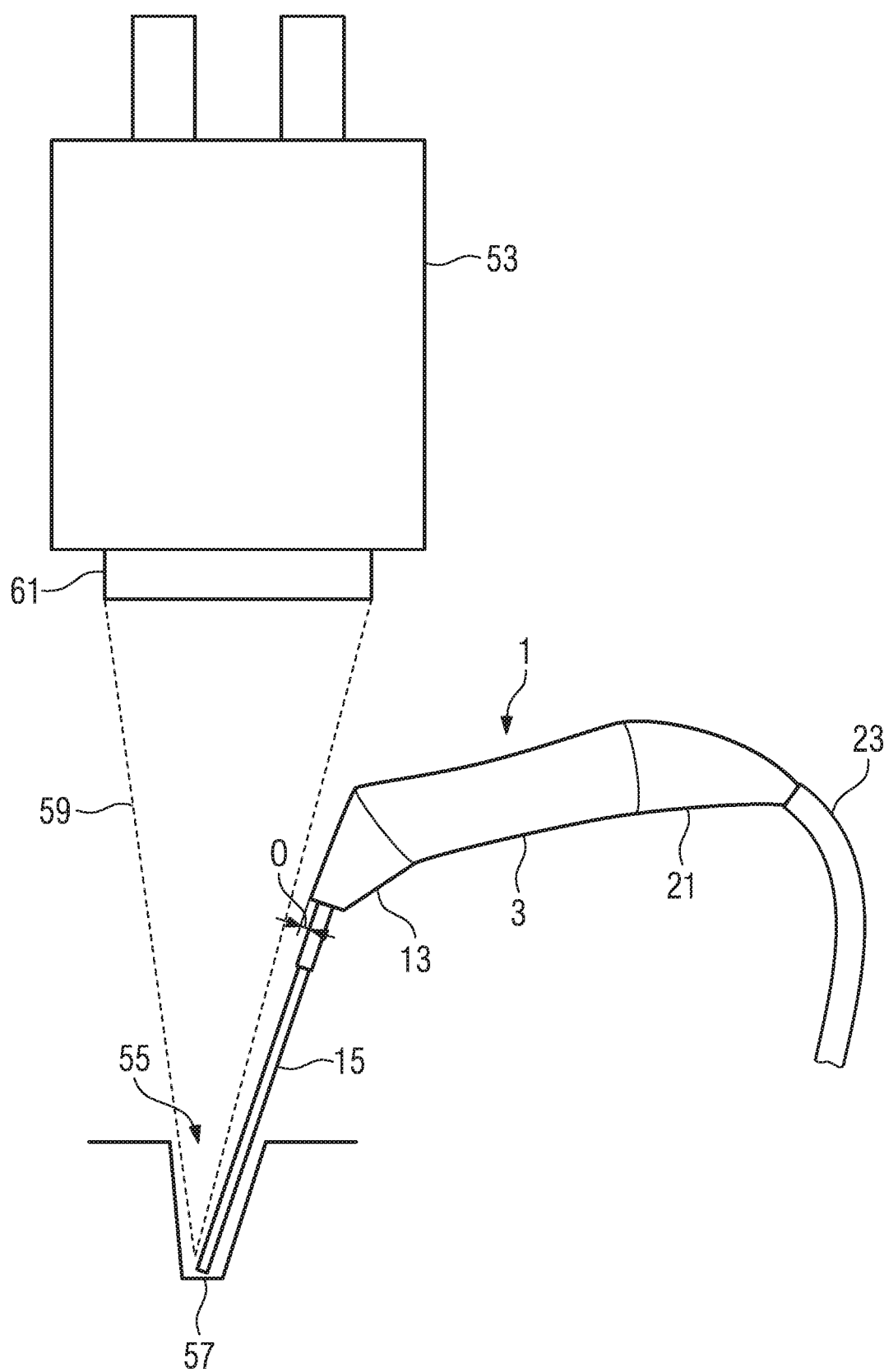
FIG. 5 shows an example of use of the endoscopic probe together with a surgical microscope.

The use of an endoscopic probe according to the invention together with a surgical microscope 53 is shown schematically in FIG. 5. In the example shown in FIG. 5, images from the bottom 57 of an operating channel 55 are captured with the aid of the shaft 15 of the endoscopic probe. At the same time, during the handling of the endoscopic probe, the operating channel 55 is viewed with the surgical microscope 53 in order to monitor the movement of the shaft 15 in the operating channel 55. It is important here that the endoscopic probe does not collide with the surgical microscope 53 during a movement inside the operating channel 55, for example during a rotation about the shaft axis AS, during insertion into the operating channel 55 or during withdrawal from the operating channel 55. Such a collision may be obtained by the described angled geometry of the shaft 15, the grip portion 3 and the rear end 21. The rear end 21, arranged at an angle to the grip portion 3, allows the cable 23, emerging from the rear end 21 in the present exemplary embodiment, to be expediently passed across the back of the hand.

To ensure that the handle 1, and in particular the front end 5, causes the least possible concealment of the viewing region observed with the surgical microscope 53, the front end 5, in a direction perpendicular to the shaft axis AS, has a protrusion O that is dimensioned such that the angle θ (cf. FIG. 1) between an imaginary line emerging from the distal end 19 of the shaft 15, extending in the plane of the shaft axis AS, the rear end axis AK and the grip portion axis AG and tangent to the front end 5 of the handle is not more than 8 degrees, preferably not more than 5 degrees. For this purpose, the protrusion O in the present exemplary embodiment can correspond at most to one tenth, in particular at most one fifteenth, and preferably at most one twentieth of the shaft length LS. In the present exemplary embodiment, the protrusion measures 5 mm at a shaft length of 120 mm, which corresponds to a twenty-fourth of the shaft length. The angle θ is 3 degrees. As is indicated in FIG. 5, it is thus possible to ensure that the opening cone 51 of the observation beam path leading to the main objective 61 is shaded only very slightly, if indeed at all, by the endoscopic probe.

It is also possible to choose the direction of the shaft axis AS such that the distal end 19, in relation to the point where the proximal end 17 joins the front end 5 of the handle 1, is offset in the radial direction by the protrusion O, such that the front end 5 obstructs the view of the distal end of the shaft 15 even less.

In the present exemplary embodiment, the shaft 15 and the handle 1, including the connection between the shaft 15 and the handle 1, are impervious to liquid and gas. Moreover, the shaft 15 and the handle 1 are made of a material that can be sterilized in an autoclave. By virtue of the fact that the endoscopic probe is impervious to liquid and gas, the components arranged in the interior of the handle and of the shaft are protected during treatment in the autoclave, such that they are not damaged by the treatment. It is thus possible to work without drapes.

In the described embodiment the angle α has been 130 degrees, the angle β has been 130 degrees, and the angle γ has been 80 degrees. In another embodiment the angle α is 120 degrees, the angle β is 120 degrees, and the angle γ is 60 degrees.

Figure 6:
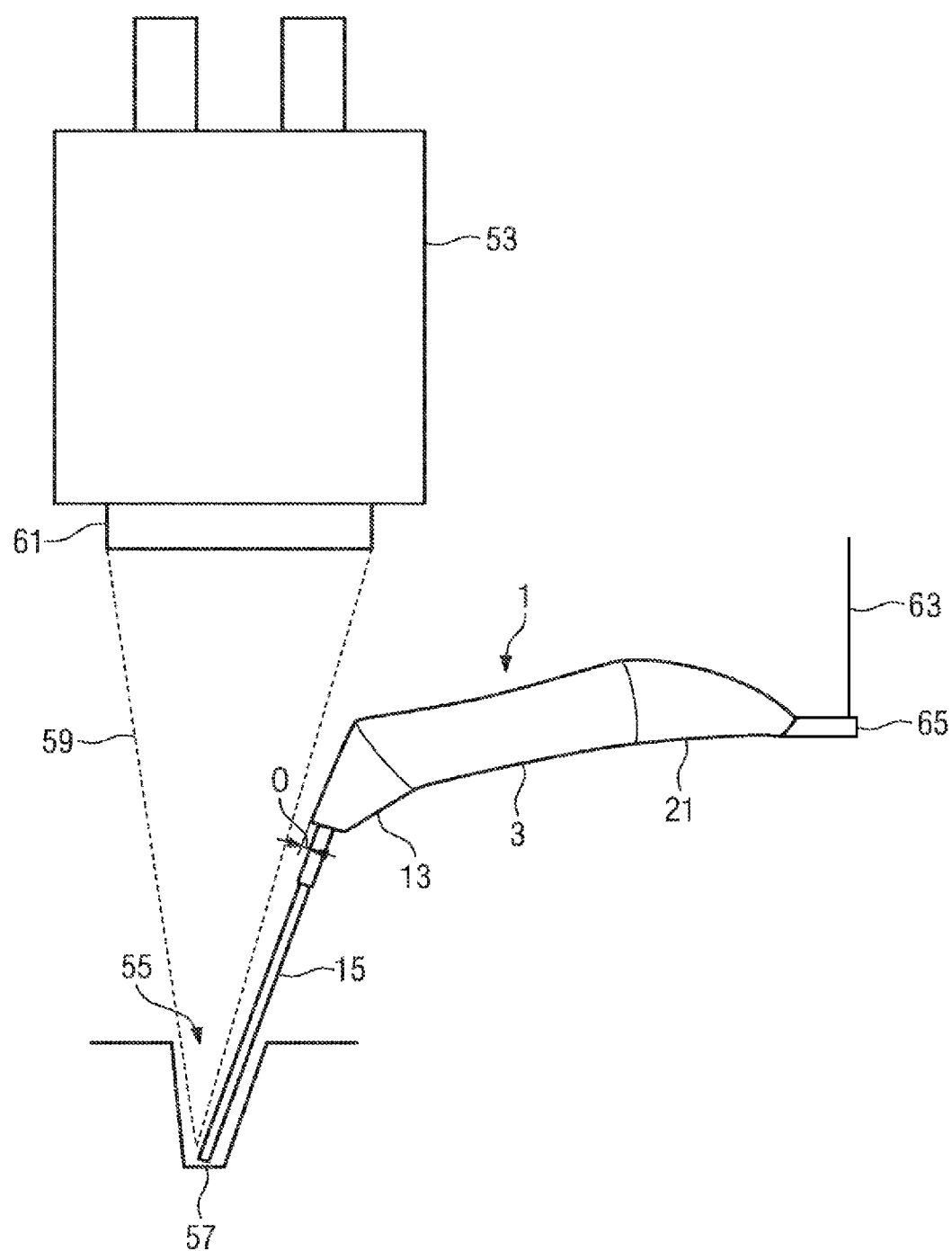
FIG. 6 shows another example of use of the endoscopic probe together with a surgical microscope.

The present invention has been described in detail on the basis of an exemplary embodiment for explanatory purposes. However, a person skilled in the art will appreciate that it is possible to depart from this exemplary embodiment. For example, the shaft, which is straight in the exemplary embodiment, may also be slightly curved, in which case the angles to the other axes are then determined using the orientation of the shaft axis in its portion directly adjoining the shaft portion of the handle. Further departures from the exemplary embodiment are possible, as has already been stated at various places in the description of the exemplary embodiment. Moreover, the endoscopic probe can be configured without cables, in which case data can then be transmitted, for example, via WLAN, Bluetooth or infrared transmission. In this case, for example, the rear end accommodates an antenna 63 (FIG. 6) for wireless transmission, and/or an accumulator 65 (FIG. 6) that supplies the energy required for the transmission. It is then possible to do without a sterilizable cable. The invention is therefore not intended to be limited to the exemplary embodiment with cable, but only to an endoscopic probe as claimed in the attached claims.

LIST OF REFERENCE SIGNS 1 handle
3 grip portion
5 front end
7 rear end
9 end face
11 end face
15 shaft
17 proximal end
19 distal end
21 rear end
23 cable
25 point of intersection
26 distal portion
27 proximal portion
29 light source 31 optical fibre
33 fibre bundle
35 digital image sensor
37 cross-sectional upper side
39 cross-sectional underside
41 convex central portion
43a, b straight portion
44a,b edge
45 apex of triangle
47 central region
49a, b straight portion
51 flatter underside
53 surgical microscope
55 operating channel
57 bottom
59 opening cone
61 main objective
63 antenna
65 accumulator
AG grip portion axis
AK rear end axis
AS shaft axis
DD external diameter
DP external diameter
DWD wall thickness
DWP wall thickness
LS shaft length
LP length of proximal portion

The invention claimed is:

1. An endoscope probe comprising:
a handle with a front end, a rear end with a rear end axis (AK) and, extending between the front end and the rear end, a straight grip portion with a grip portion axis (AG);
a shaft extending from the front end of the handle and having a shaft axis (AS),
wherein
the shaft axis (AS), the rear end axis (AK) and the grip portion axis (AG) lie within a common plane,
the shaft axis (AS) encloses an angle ($\alpha$) in the range of 100 to 140 degrees with the grip portion axis (AG),
the grip portion axis (AG) encloses an angle ($\beta$) in the range of 110 to 130 degrees with the rear end axis (AK),
the shaft axis (AS) encloses an angle ($\gamma$) in the range of 30 to 90 degrees with the rear end axis (AK),
the grip portion in a plane perpendicular to the common plane of the shaft axis (AS), the grip portion axis (AG), and the rear end axis (AK) has a cross section with a cross-sectional upper side that forms the side of the handle facing the point of intersection of an imaginary continuation of the shaft axis (AS) with an imaginary continuation of the rear end axis (AK) and a cross-sectional underside facing away from the cross-sectional upper side, and
the cross-sectional upper side has a central portion and, adjoining the central portion, two straight portions which form cut-outs from limbs of an imaginary isosceles triangle whose apex lies centrally above the cross-sectional upper side.

2. The endoscope probe according to claim 1, in which the angle that the shaft axis (AS) encloses with the grip portion axis (AG) is the same size as the angle that the grip portion axis (AG) encloses with the rear end axis.

3. The endoscope probe according to claim 1, in which the shaft has a length in the range of 110 to 130 mm.

4. The endoscope probe according to claim 1, in which the shaft has a diameter in the range of 3.0 to 4.1 mm.

5. The endoscope probe according to claim 1, in which the shaft has a wall thickness in the range of 0.3 to 0.5 mm, at least in a distal portion.

6. The endoscope probe according to claim 1, in which the shaft has a proximal portion with a wall thickness in the range of 1.3 to 1.5 mm, which proximal portion adjoins the front end of the handle.

7. The endoscope probe according to claim 6, in which the proximal portion has a length in the range of 10 to 20 mm.

8. The endoscope probe according to claim 1, in which the grip portion has a diameter in the range of 18 to 38 mm.

9. The endoscope probe according to claim 1, in which the grip portion and the front end together have a length (LH) in the range of 100 to 120 mm.

10. The endoscope probe according to claim 1, in which the cross-sectional underside has a convexity, wherein the cross-sectional underside has a central region with a central convexity and, adjoining the central region, portions that have a lesser convexity compared to the central convexity.

11. The endoscope probe according to claim 1, in which the side of the grip portion formed by the cross-sectional underside has a bearing surface for the middle finger.

12. The endoscope probe according to claim 1, in which the shaft is arranged at the front end of the handle in such a way that the front end perpendicularly with respect to the direction of extent of the shaft axis (AS), has a maximum protrusion, over the shaft that is dimensioned such that the angle $\theta$ between the shaft axis and an imaginary line emerging from the distal end of the shaft extending in the plane of the shaft axis (AS), the rear end axis (AK) and the grip portion axis (AG) and tangent to the front end of the handle is not more than 8 degrees.

13. The endoscope probe according to claim 12, in which the interior of the shaft accommodates an image-conveying optics system with which object light emanating from an object observed by means of the endoscopic probe is conveyed to an image sensor arranged in the handle.

14. The endoscope probe according to claim 12, in which the interior of the handle accommodates a light source for emitting illumination light with which the object observed by means of the endoscopic probe is illuminated, and in which an optical fibre for conveying the illumination light to the object observed by means of the endoscopic probe extends through the interior of the shaft.

15. The endoscope probe according to claim 1, in which the shaft and the handle, including a connection between the shaft and the handle, are impervious to liquid and gas, and the shaft and the handle are made of a material that can be autoclaved.

16. The endoscope probe according to claim 1, in which the rear end is a cable outlet end with an emerging cable wherein the cable emerges from the cable outlet end at an angle of not more than 20 degrees with respect to the rear end axis (AK).

17. The endoscope probe according to claim 16, in which the connection between the cable outlet end and the cable is impervious to liquid and gas, and the cable is made of a material that can be autoclaved.

18. The endoscope probe according to claim 1, in which the rear end contains an antenna and/or an accumulator.

* * * * *